United States Patent
Bol et al.

(10) Patent No.: US 7,067,827 B2
(45) Date of Patent: Jun. 27, 2006

(54) APPARATUS AND METHOD FOR ELECTRON BEAM IRRADIATION HAVING IMPROVED DOSE UNIFORMITY RATIO

(75) Inventors: Jean Louis Bol, Genappe (BE); Olivier Gregoire, Louvain-la-Neuve (BE); Francis Martin, Conflans-Ste-Honorine (FR); Benoît Mullier, Grand-Leez (BE); Frédéric Stichelbaut, Mazy (BE)

(73) Assignee: Ion Beam Applications S.A. (BE)

( * ) Notice: Subject to any disclaimer, the term of this patent is extended or adjusted under 35 U.S.C. 154(b) by 0 days.

(21) Appl. No.: 10/902,394

(22) Filed: Jul. 28, 2004

(65) Prior Publication Data
US 2005/0098740 A1    May 12, 2005

(30) Foreign Application Priority Data
Jul. 30, 2003    (EP) .................................. 03447202

(51) Int. Cl.
*G01N 9/04*    (2006.01)
(52) U.S. Cl. ................ 250/492.2; 250/394; 250/453.1; 250/337; 250/305; 250/434; 250/400; 53/167; 53/426; 141/85
(58) Field of Classification Search ............. 250/492.2, 250/394, 453.1, 337, 305; 53/167, 426; 141/85
See application file for complete search history.

(56) References Cited

U.S. PATENT DOCUMENTS

| 4,010,374 A | | 3/1977 | Ramler |
| 4,324,813 A | * | 4/1982 | Sonnenberg ................ 427/496 |
| 4,983,849 A | | 1/1991 | Thompson et al. |
| 5,809,739 A | | 9/1998 | Eno |
| 5,825,037 A | * | 10/1998 | Nablo ...................... 250/492.3 |
| 6,833,551 B1 | * | 12/2004 | Avnery ..................... 250/492.3 |

FOREIGN PATENT DOCUMENTS

| JP | 08322914 | 12/1996 |
| WO | 98/24484 | 6/1998 |

\* cited by examiner

*Primary Examiner*—Nikita Wells
*Assistant Examiner*—Zia R. Hashmi
(74) *Attorney, Agent, or Firm*—Fitch, Even, Tabin & Flannery (57) ABSTRACT

The present invention is related to an apparatus and method for irradiating a product package, comprising a radiation source directing a radiation beam along a beam direction towards said product package, conveying means for transporting said product package past said radiation source along a transport path, and reflecting means located on at least one side of the plane formed by said beam direction and said transport path. By adjusting the distance and angle of the reflecting means to the conveyor and beam, and improved dose uniformity ratio is obtained.

11 Claims, 11 Drawing Sheets

APPARATUS AND METHOD FOR ELECTRON BEAM IRRADIATION HAVING IMPROVED DOSE UNIFORMITY RATIO

FIELD OF THE INVENTION

The present invention is related to an apparatus and method for electron beam irradiation wherein an improved dose uniformity ratio in irradiated products can be obtained.

STATE OF THE ART

Irradiation is used to treat many types of products and articles, e.g. for sterilising medical devices, or for pasteurising food. Irradiation is also used for polymerization of liquid monomers or degradation or cross-linking of polymers.

Depending on the level of dose required for achieving an effect, and the type of irradiation source available, one uses gamma rays, electron beams or x-rays. These radiation types have very different properties as to penetration in matter, and the production methods are also very different (see "Radiation Sterilization for Health Care Products", B. P. Fairand, CRC Press, 2002).

An irradiation process is often specified by a minimum absorbed dose to achieve the desired effect and a maximum dose limit that the product can tolerate while still being functional (see ISO/ASTM 51649 and ISO/ASTM 51702). The dose distribution within a product is characterized by the Dose Uniformity Ratio (DUR), defined as the ratio of the maximal to the minimal dose absorbed in the product, and depends on process load characteristics, irradiation conditions and operating parameters.

Due to the non-uniformity of dose in the product (high DUR), a given product may not be treatable at a given facility because the maximum acceptable dose would be exceeded at some place while the lowest dose in the product is at the lower limit.

Figure 1:
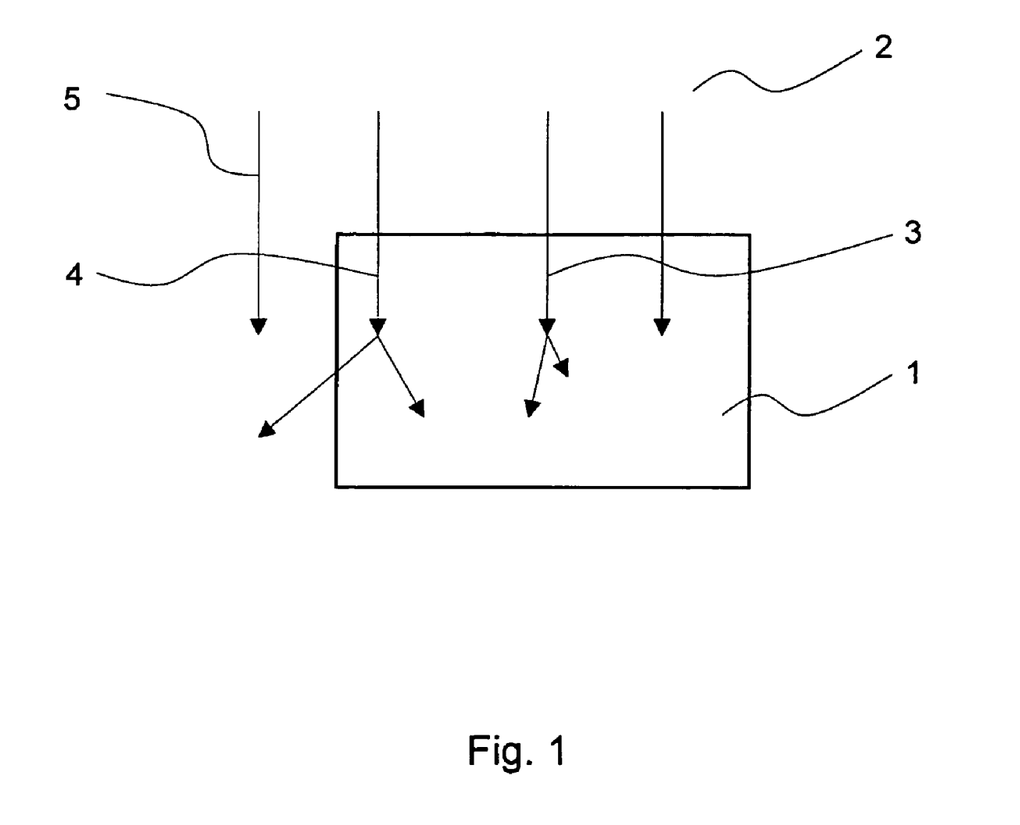
FIG. 1 represents a parallel electron beam impinging on a product package and different electron paths in the beam.

When a homogenous package of material is irradiated with an electron beam, one observes the so-called "side-effect" problem: the absorbed dose measured at the side faces is lower than the dose measured in the middle of the package. This can be explained as follows, with reference to FIG. 1: when a slab of material 1 is irradiated from above with a parallel beam 2 of electrons, electrons in the material are scattered several times and produce a shower of electrons in all directions around the initial beam. These electrons progressively lose their energy, and consequently deposit some dose in the material. Electrons 3 falling in the central area of the slab of material either deposit energy in the original direction, or are scattered in the surrounding material and deposit their energy in the material. Some of the electrons 4 falling near the edges of the slab are scattered outside of the slab, in the air, and are lost, because they go on on a straight path, and are never scattered back into the material by the air. Any electron 5, having a path in the air near the side of the slab of material will not be scattered by the air into the slab of material, and therefore will not contribute to the dose in the product.

Figure 2:
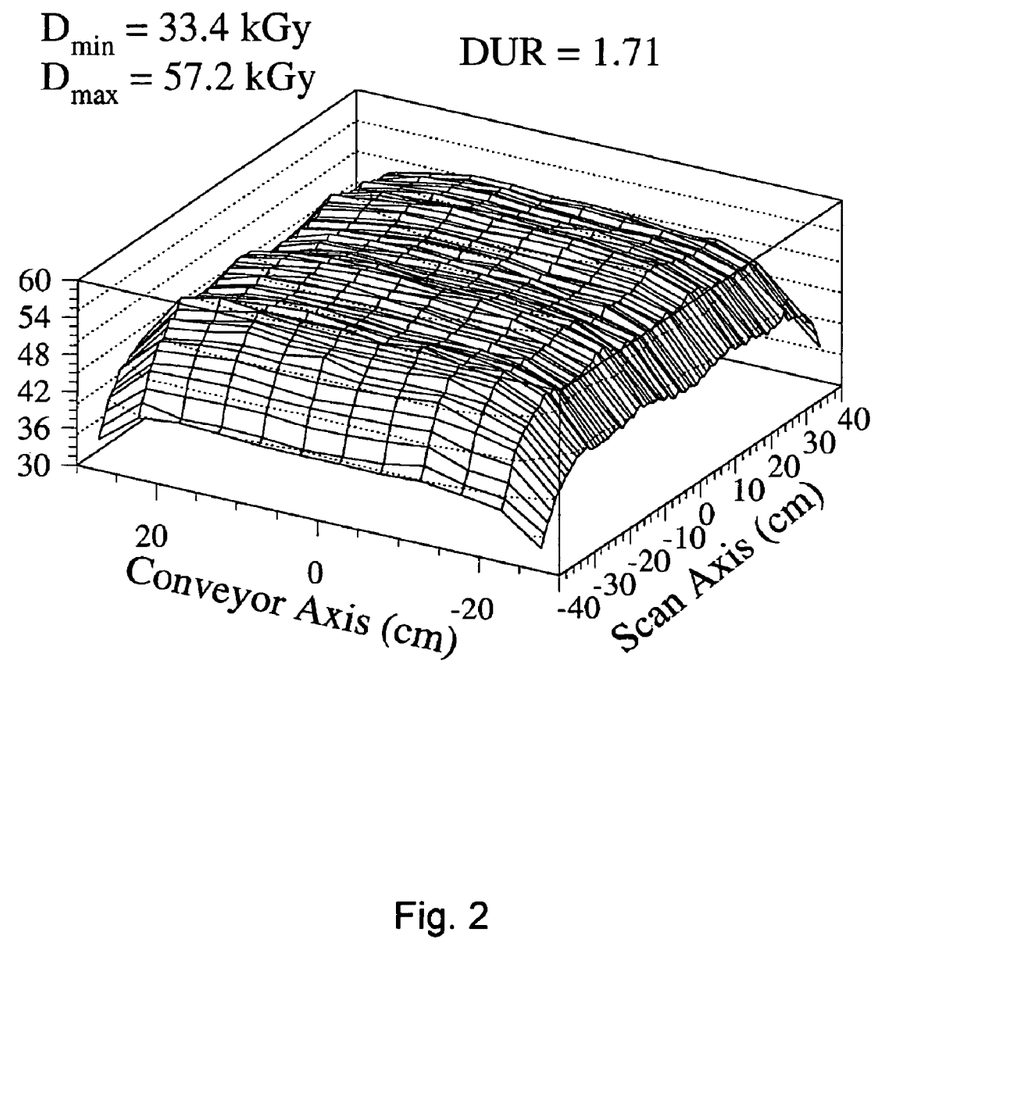
FIG. 2 represents the dose distribution in a horizontal plane in a product package.

Irradiation apparatuses usually comprise an electron accelerator producing a thin electron beam, a scanning magnet for producing a fan-shaped beam in a plane, and a conveyor system for transporting product packages past the fan-shaped beam, in a direction perpendicular to the beam plane. The fan shaped beam may either immediately be directed towards the product package, as a diverging beam, or be submitted to a magnetic field for obtaining a parallel beam. FIG. 2 illustrates the measurement of dose distribution in the bottom layer of a parallelepipedal product package obtained in a parallel electron beam irradiation apparatus according to the state of the art. A product package having a length of 60 cm along the conveyor direction, and a width of 80 cm along the scan direction is irradiated from above, during the transport. A maximum dose Dmax of 57.2 kGy is obtained in the central area, surrounded by a substantially flat plateau. One observes a dose fall-off on the sides along the conveyor direction as well as on the sides along the scan direction. The minimum dose Dmin is obtained in the corners, at 33.4 kGy, leading to a DUR ratio of 1.71. In this configuration, the above side-effect may be limited by having product packages in close contact to each other in the conveyor direction. However, this requires a control system for the conveyor ensuring successive product packages are in contact with each other, including the first and last package of a batch of packages, and the side-effect remains for the sides of the product package along the conveyor direction.

Document WO 90/09667 discloses an irradiation device wherein a magnetic lens transforms a diverging fan-like beam into a parallel (or even converging) beam. This solution may improve homogeneity (i.e. provide a lower DUR), but one still observes the side effect, i.e. a dose fall-off on the lateral sides of the package. In said device, the irradiation is performed from below.

Document EP 0 891 192 B1 discloses an irradiation device having an irradiation source irradiating a product package from above, wherein an absorption trap, located below the product package, comprises a particle reflecting body including cooling means. The purpose of said reflecting body is to scatter the electrons that emerge at the bottom back to the product package. In a preferred embodiment of this irradiation device, the reflecting body is in the shape of a "U", with a lower part and two side walls standing up at the respective ends of the lower part. However, this design is far from optimal in the reduction of the side effect, i.e. one still observes a dose fall-off on the lateral sides of the package. Moreover, this device lacks versatility in that it cannot be adapted to packages of variable widths.

Document U.S. Pat. No. 4,983,849 discloses an apparatus and method for promoting uniform dosage of ionizing radiation in targets. In said apparatus, a scatter plate is located between the accelerator window and a product package for induced radiation scatter. According to the document, an improvement in the dose uniformity is thereby obtained. In a preferred version of this apparatus, the product package is placed in a radiation-reflecting basket for increasing dose at the periphery on the product package. Angled side scatter plates are positioned along the four sides of the basket. The preferred range of angles for said plates is between 23 and 68 degrees, and preferably, 45 degrees. However, this apparatus neither provides a good throughput nor a significantly improved DUR. Because of the scatter plate, a significant fraction of the accelerator power is lost in the scatter plate. The use of radiation reflecting baskets for supporting the product packages in their travel below the accelerator implies the design of a larger conveyor path, and therefore a larger shielding. Obviously, the sizes of the product packages and the reflecting baskets must match, which limits the flexibility of said apparatus and method. The presence of angled side scatter plates along the front and rear side of the product package in the direction of conveyor travel additionally reduces the throughput of this installation. Moreover, the selection of the angles of the angled side scatter plates is far from optimal.

AIMS OF THE INVENTION

The present invention aims to provide an irradiation apparatus and method which do not present the drawbacks of the apparatuses and methods of the state of the art mentioned hereabove.

More precisely, the present invention aims to provide an irradiation apparatus wherein the side effect is minimized, without impairing throughput, without losing flexibility, i.e. capable of handling products of different sizes, densities, dose requirements, and without increasing running and building costs.

SUMMARY OF THE INVENTION

The present invention is related to an apparatus for irradiating a product package, comprising a radiation source directing a radiation beam along a beam direction towards said product package, conveying means for transporting said product package past said radiation source along a transport path, and reflecting means located on at least one side of the plane formed by said beam direction and said transport path. The reflecting means are at an angle of 1 to 15 degrees relative to the beam direction, and converging therewith. By using these reflectors, part of the electrons are directed to the sides of the product package, thereby improving the dose uniformity ratio (DUR). Preferably the radiation source is an electron beam source. By providing means for adjusting the distance to the transport path and/or the angle of the reflecting means with respect to the beam direction, an optimal configuration can be obtained, with an improved DUR. The reflecting means may be one or more rectangular metal sheets. In another embodiment of the invention, the reflecting means comprises a plurality of scales, preferably oriented perpendicularly to said beam direction. Said reflecting means may preferably comprise means for cooling. Advantageously, the conveying means are provided with a gap under the radiation beam, and the reflecting means are positioned in said gap. It is known to provide a gap in the conveyor under the beam, in order to protect the mechanics of the conveyor from constant radiation. The reflectors may then extend in said gap, below the bottom layer of the product package.

The present invention is also related to a method for irradiating product packages, comprising the steps of:
- providing a radiation source directing a radiation beam towards a transport path;
- providing reflecting means for reflecting part of said radiation beam towards said transport path;
- adjusting the angle of said reflection means to the radiation beam;
- transporting said product package along said transport path, under said radiation beam, whereby part of said radiation beam is reflected on sides of said product package.

Preferably, the method comprises the step of adjusting the distance of said reflection means to said transport path according to the size of the product package, for minimizing the distance between said reflection means and said product package.

The present invention is also related to the use of an apparatus or of a method according to the invention for irradiating product packages having a mean density comprised between 0.05 and 0.50 g/cm3.

When energetic electrons impinge on a slab of material, a fraction of these electrons is transmitted, a fraction is stopped, and a fraction is backscattered. The fraction of backscattered electrons is larger for higher Z materials. Backscattered electrons have an angular distribution with a broad peak in the backward direction (i.e. at 180° from the initial beam direction) (T. Tabata, *Backscattering of Electrons* from 3.2 to 14 MeV, Phys. Rev., 162, 336 (1967)). The backscattered electrons have an energy distribution spectrum below the energy of the initial electrons (D. H. Rester and J. H. Derrickson, *Electron Backscatter Measurements for Perpendicular and Non-Perpendicular Incidence at 1.0 MeV Bombarding Energy*, Nucl. Instr. And Meth. 86, 261 (1970)). In the present patent application, the words "reflecting means" or "reflector" must be understood as means providing a fraction of backscattered electrons, with a broad angular distribution in the backward direction, and a broad energy spectrum. It is not to be understood in the common optical sense, where a beam is reflected under a reflection angle equal to the incidence angle, and with same spectrum.

DESCRIPTION OF THE PREFERRED EMBODIMENTS OF THE INVENTION

Figure 3:
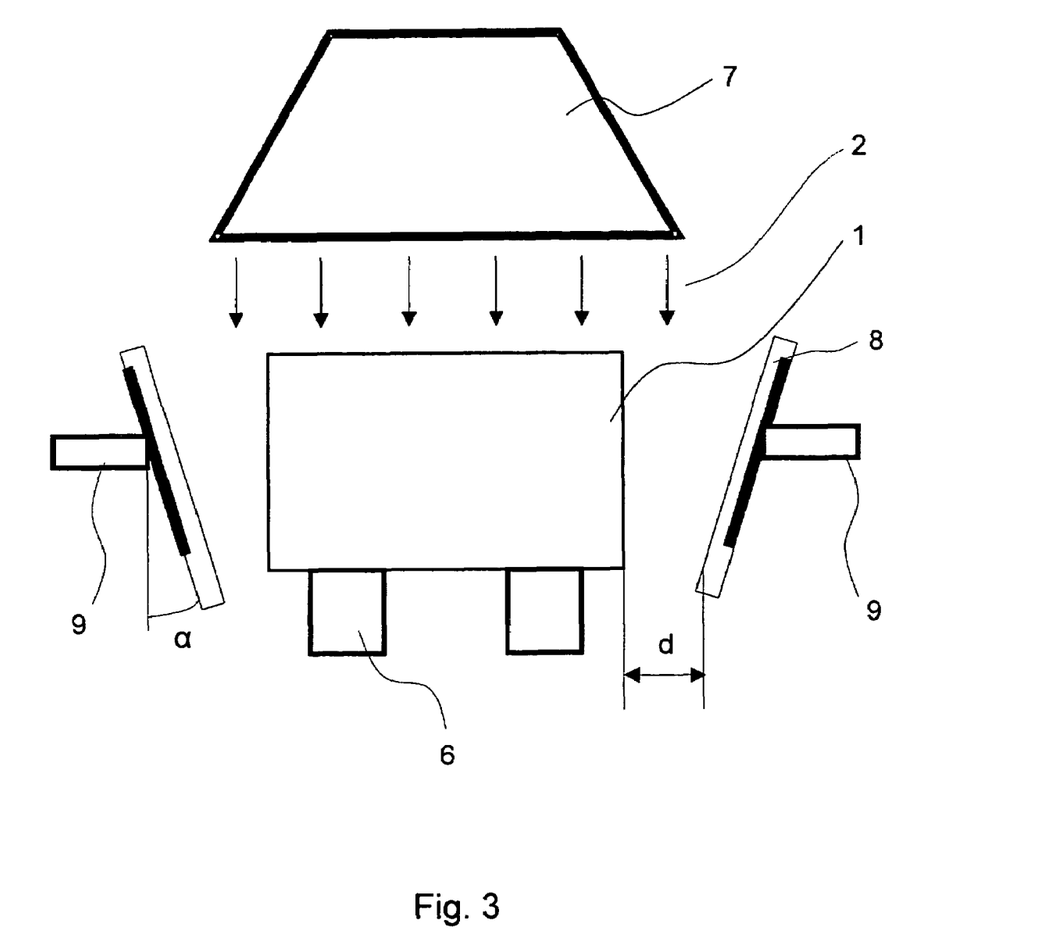
FIG. 3 represents a section view perpendicular to the transport path of a proposed design according to the invention.

FIG. 3 represents a section view with the section taken perpendicular to the transport path of a first embodiment according to the invention. A product package 1 is transported by a conveyor 6. The conveyor 6 may be any conventional conveyor system, such as a chain conveyor or a roller conveyor. Motor means and control means are provided for transporting the product package under the beam at a controlled speed. A scan horn 7 above the product package provides a beam of electrons, either parallel or divergent. The width of the electron beam 2 at the top layer of the product package 1 is larger than the width of the product package. Reflecting means 8 are installed on both sides of the conveyor path. These reflector means are rectangular sheets of material. Materials used for the reflectors should preferably have good electrical and thermal conduction as well as good mechanical properties. Materials with high Z will be more efficient to reflect radiations. Metallic materials with good corrosion resistance such as stainless steel will be preferred. Materials that can be activated, such as tungsten or tantalum, will be avoided. The mechanical supports 9 for the reflectors 8 allow adjustment of the distance d measured at the bottom of the product packages, and of the angle α between reflector and beam direction. Means for adjusting distance and/or angle may be screws, chains, jacks or pistons. Reflectors may be mounted on rails to ease their movement. The distance d may be adapted depending on the size of the product packages to be processed. The reflector plates may be cooled by circulation of air, water or any other fluid. The reflecting surface of the reflectors may be made from one piece of metal or several smaller pieces welded together. In one embodiment, the reflector may be made from one or several square-sectioned pipes filled with cooling fluid. Reflectors are preferably made of solid material, but may as well be a trickle or stream of liquid metal. A Process Control System (PCS) may be used to control processing parameters such as the scanning width or the beam current. In this case, the position of reflector(s) may be controlled by this PCS as a parameter, or be linked to the scanning width. The angle of the plates may also be modified and controlled by the PCS.

Figure 4:
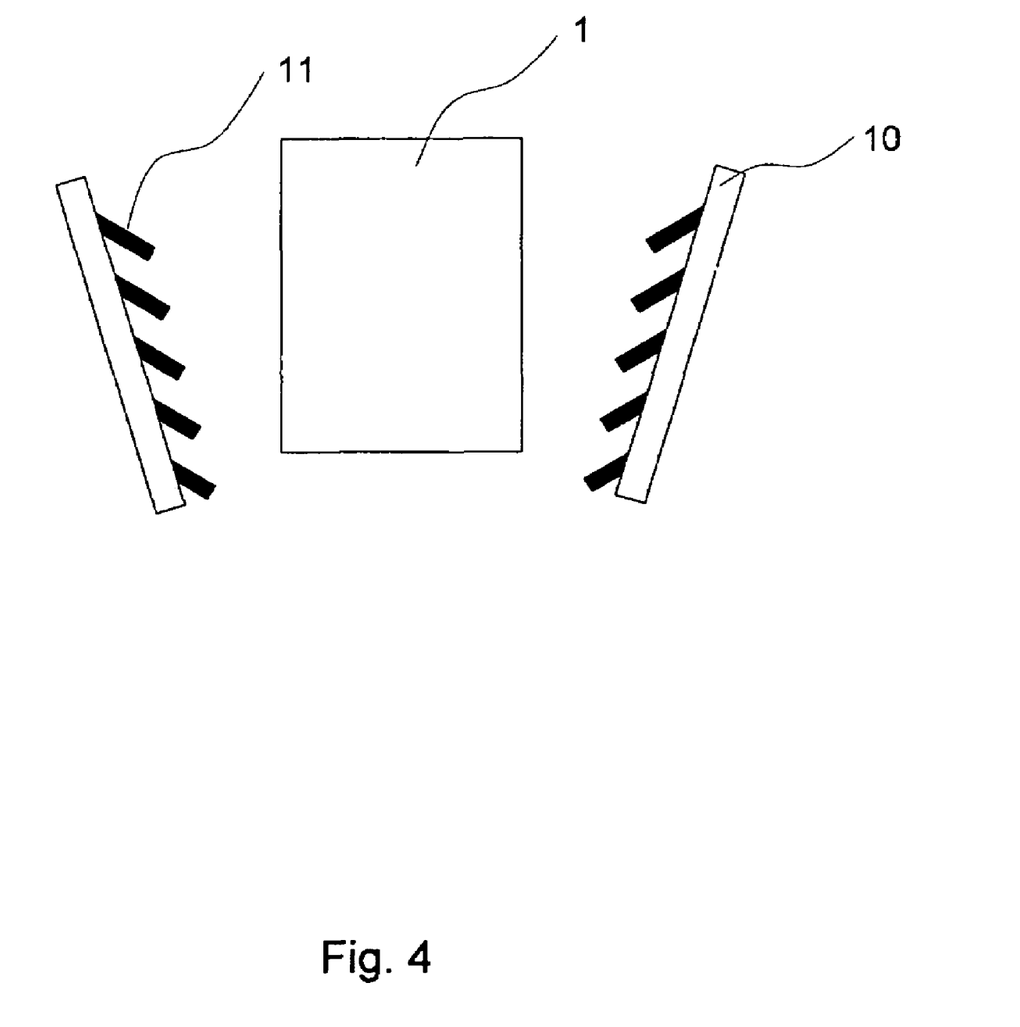
FIG. 4 represents a schematic section view of a reflector comprising scales.

FIG. 4 represents a schematic section view of another embodiment of the invention wherein the reflector comprises scales. A set of plates 11 are mounted on a support structure 10. The distance d and angle α are adjustable as in the first embodiment. In addition, the angle of the plates 11 to the support structure 10 is adjustable. Lengthwise, i.e. seen from the side of the transport path the scales 11 are perpendicular to the beam direction.

Figure 5:
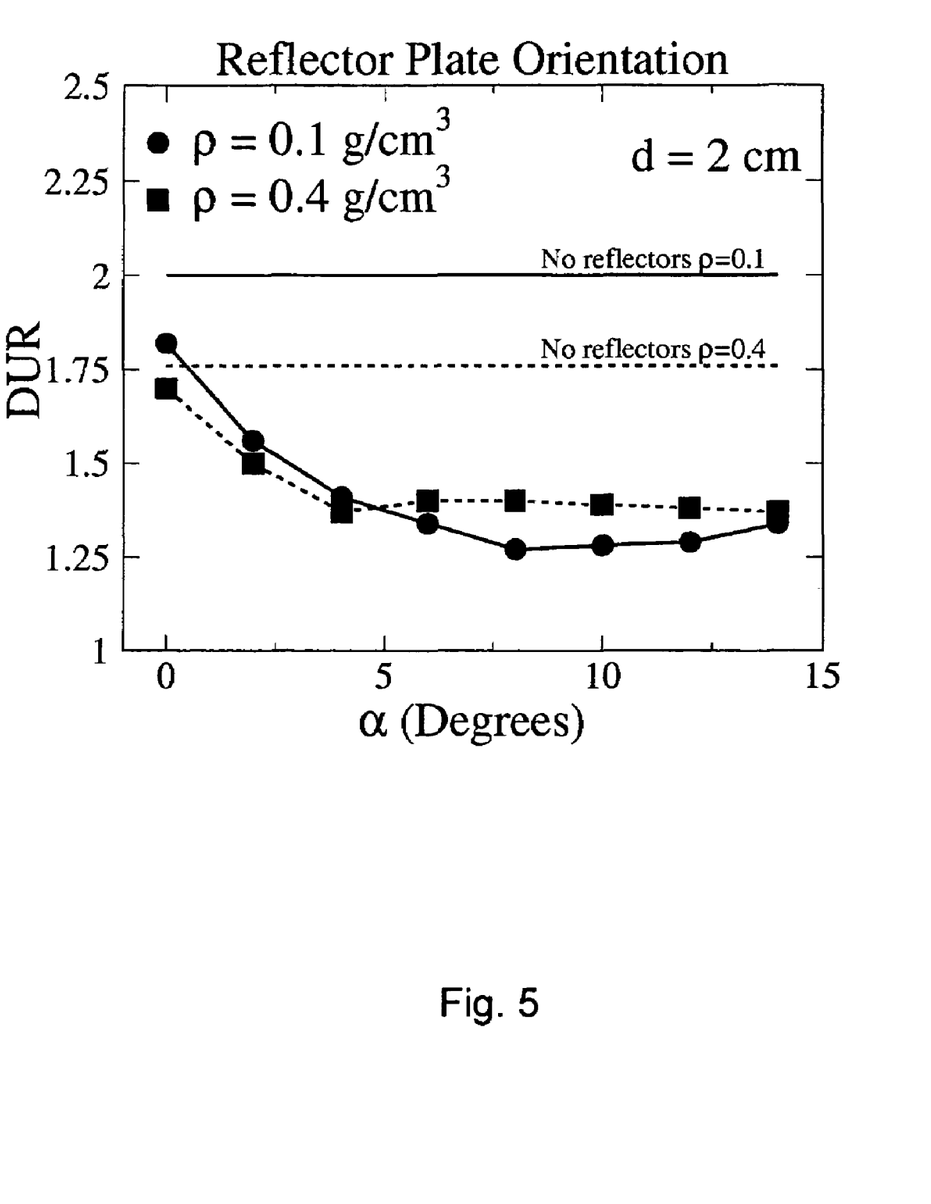
FIGS. 5 and 6 are DUR curves as a function of the angle and distance of side reflectors, respectively.
Figure 6:
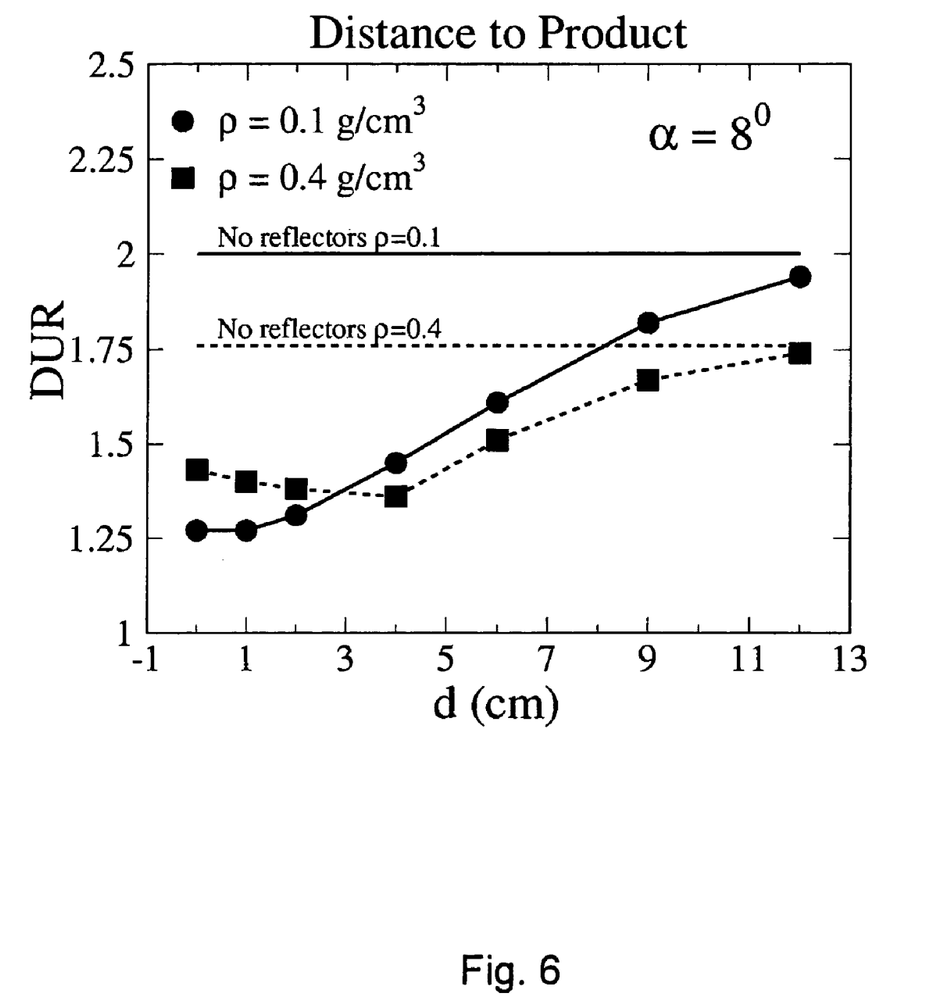

Simulation of dose deposition of an electron beam in the configuration of FIG. 3 has been performed. Monte-Carlo simulations, with the GEANT package from CERN, were obtained for various values of the parameters involved, i.e. the distance d, and the angle α, with a monoenergetic 10 MeV electron beam. FIGS. 5 and 6 are DUR curves as a function of the angle and distance of side reflectors, respectively for two densities of the product packages, 0.1 g/cm3 and 0.4 g/cm3. These densities are commonly found in the medical devices industry. FIG. 5 shows that, for a fixed distance d of 2 cm, a significant improvement is obtained with respect to the same apparatus without reflectors, and that reflectors having an angle above 2° give better results than vertical reflectors. FIG. 6 shows that, for a fixed angle of 8°, a small distance, i.e. between 0 and 4 cm, gives good results. Therefore, in many tests, the optimal value of 2 cm has been selected.

Figure 7:
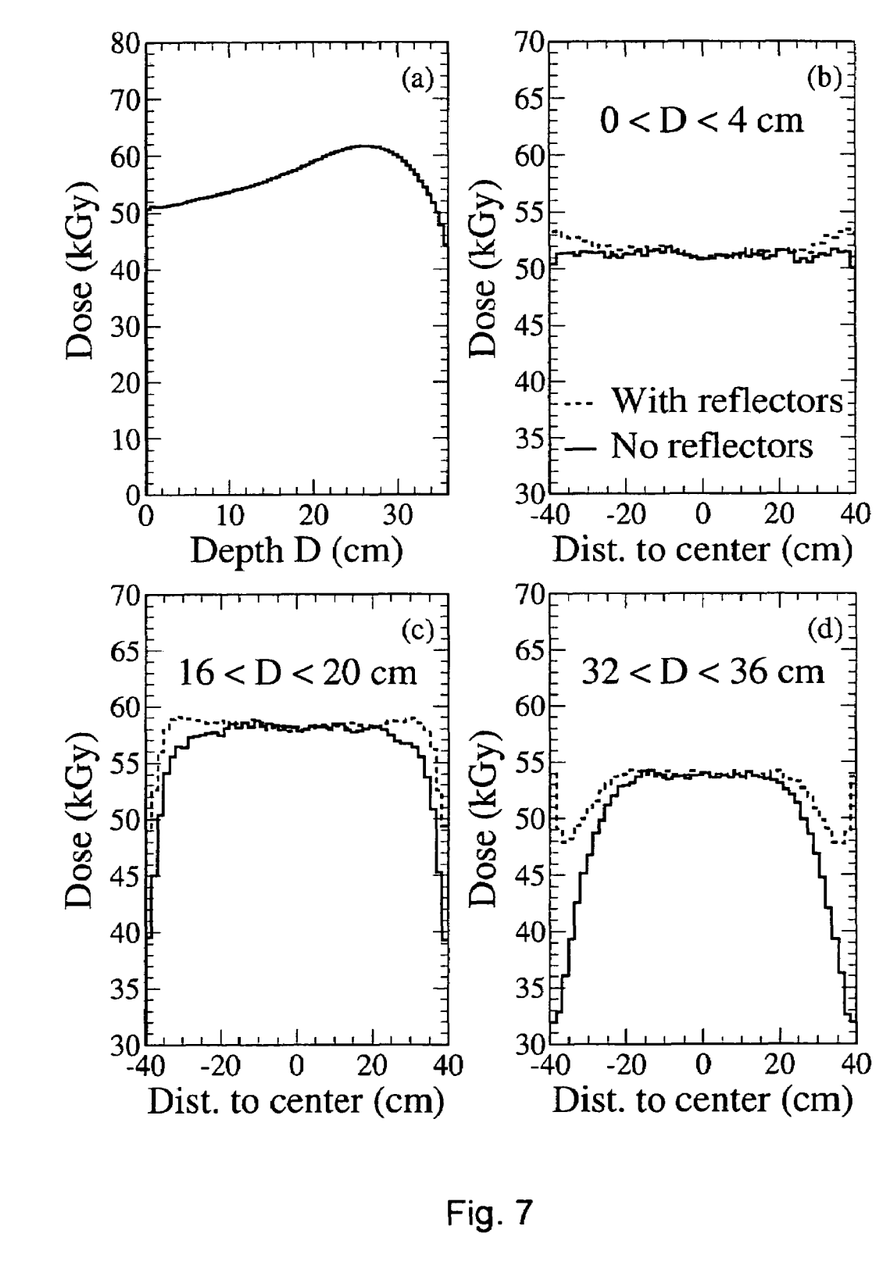
FIGS. 7a is a Dose vs. depth in the central area of a product package for a density of 0.10 g/cm3.
FIGS. 7b, 7c and 7d are dose profiles along the scan direction, in the top layer, mid-height layer, and bottom layer, respectively, of a product package having a density of 0.10 g/cm3, and a height of 36 cm.

FIG. 7a is a dose vs. depth in the central area of a product package for a density of 0.10 g/cm3. The dose, 51 kGy in the upper layer of the package, increases slowly up to a peak of 62 kGy at a depth of 28 cm, and then decreases to 44 kGY, in the bottom layer of the package, at a depth of 36 cm. A fraction of the electrons will emerge at the bottom surface of the product package, and be lost. The increase of dose under the surface is due to the generation of secondary electrons and the slowing down of primary electrons, staying longer in a given volume of product and therefore releasing more energy per unit of mass.

FIGS. 7b, 7c and 7d are dose profiles along the scan direction, in the top layer, mid-height layer, and bottom layer, respectively, of a product package having a density of 0.10 g/cm3, and a height of 36 cm. In the top layer, where the "no reflector" dose profile is flat, the reflectors produce a slight increase of the dose on the side. However, because of the selected angle, the reflectors are at some distance, and their effect is minimal. In the mid-height layer, the side effect is more significant, and the reflectors, being nearer to the product, have more effect. In the bottom layer, where the side effect is the most apparent, the reflectors, being very near to the product package, have their most important effect. A careful selection of distance and angle, for a given product density, allows to find an optimal dose uniformity ratio. Reflectors will preferably be made of flat plates of material but may be curved inward or outward, or comprise excrescences. In the embodiment with scales mounted on a frame, the angle of scales may be different from the bottom to the top in order to optimise the DUR at every depth in the product.

Figure 8A:
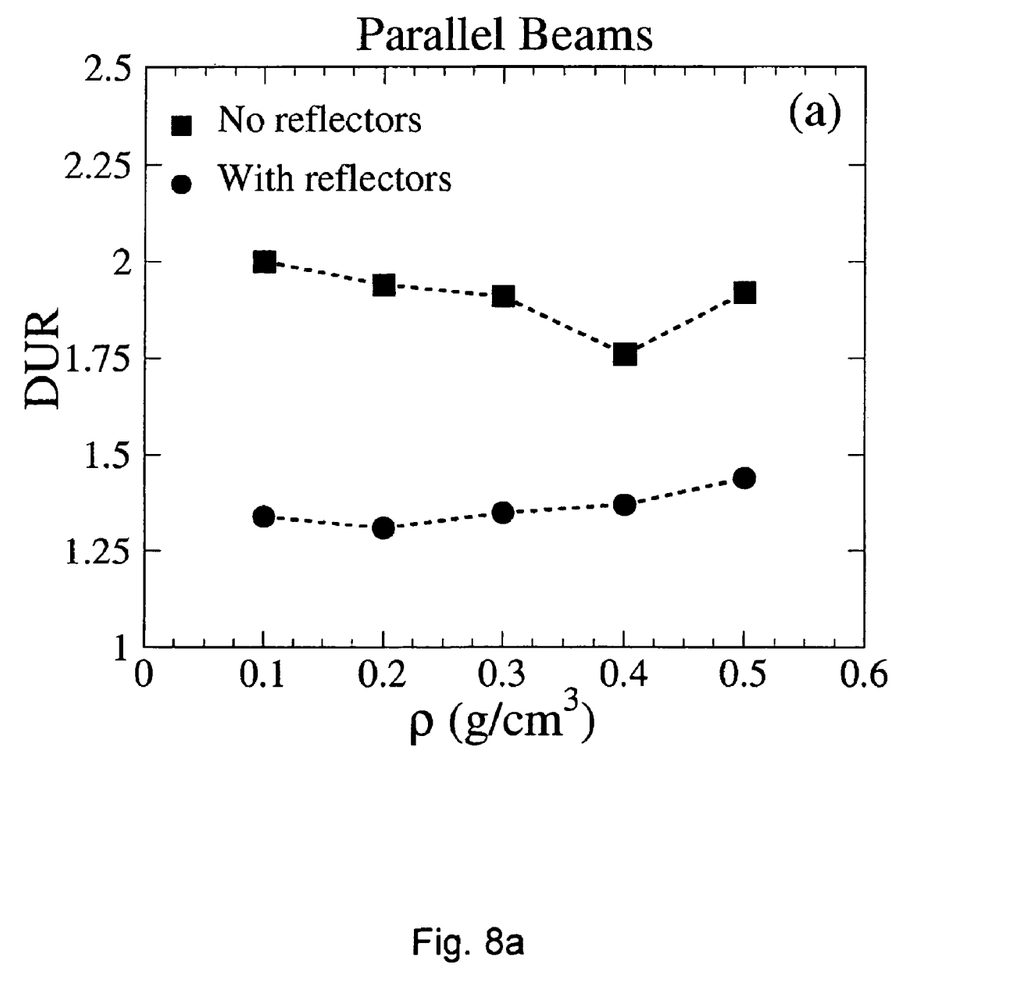
FIGS. 8a, 8b, 9a and 9b are DUR and Dmin curves as a function of the density of product packages, for a parallel and diverging electron beam, respectively.
Figure 8B:
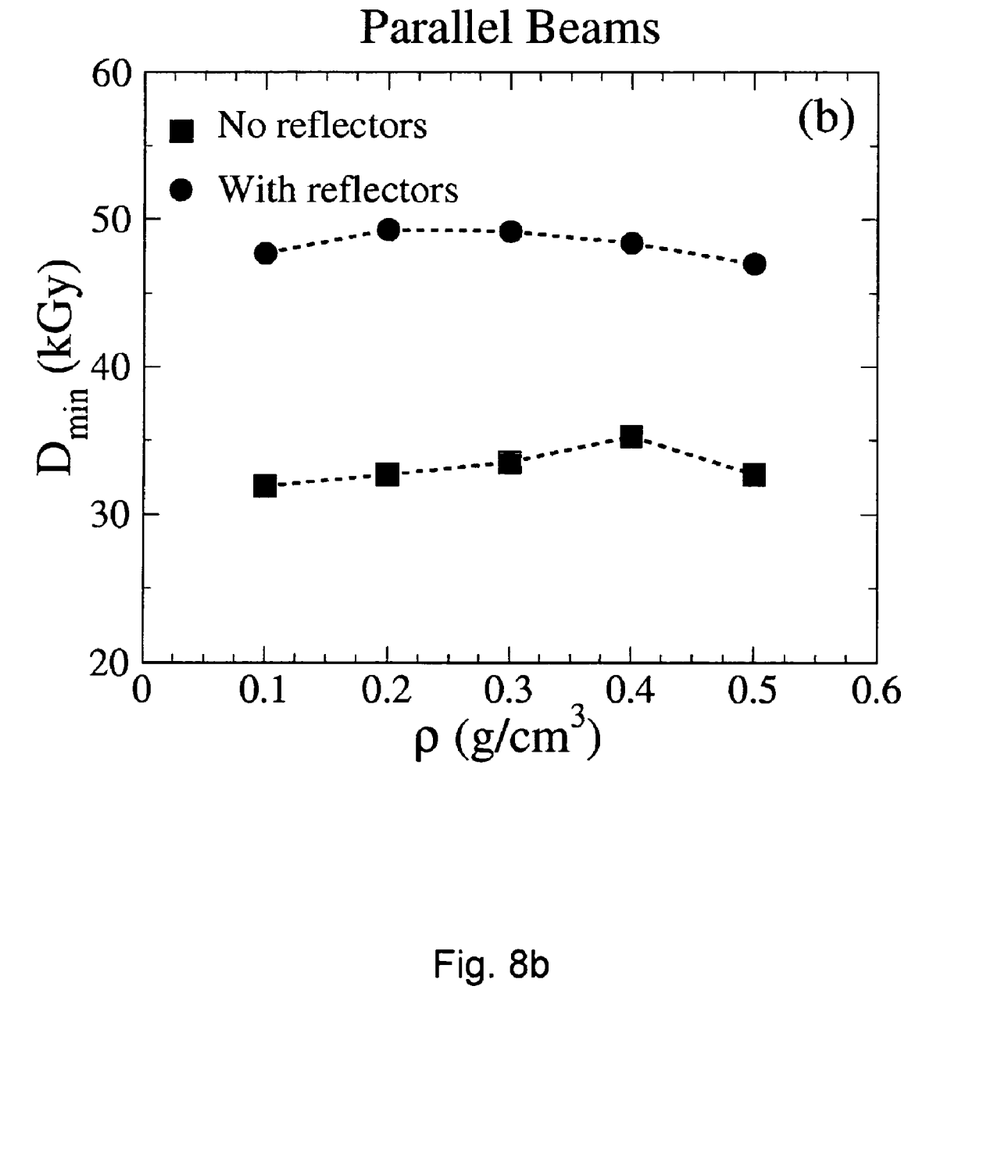
Figure 9A:
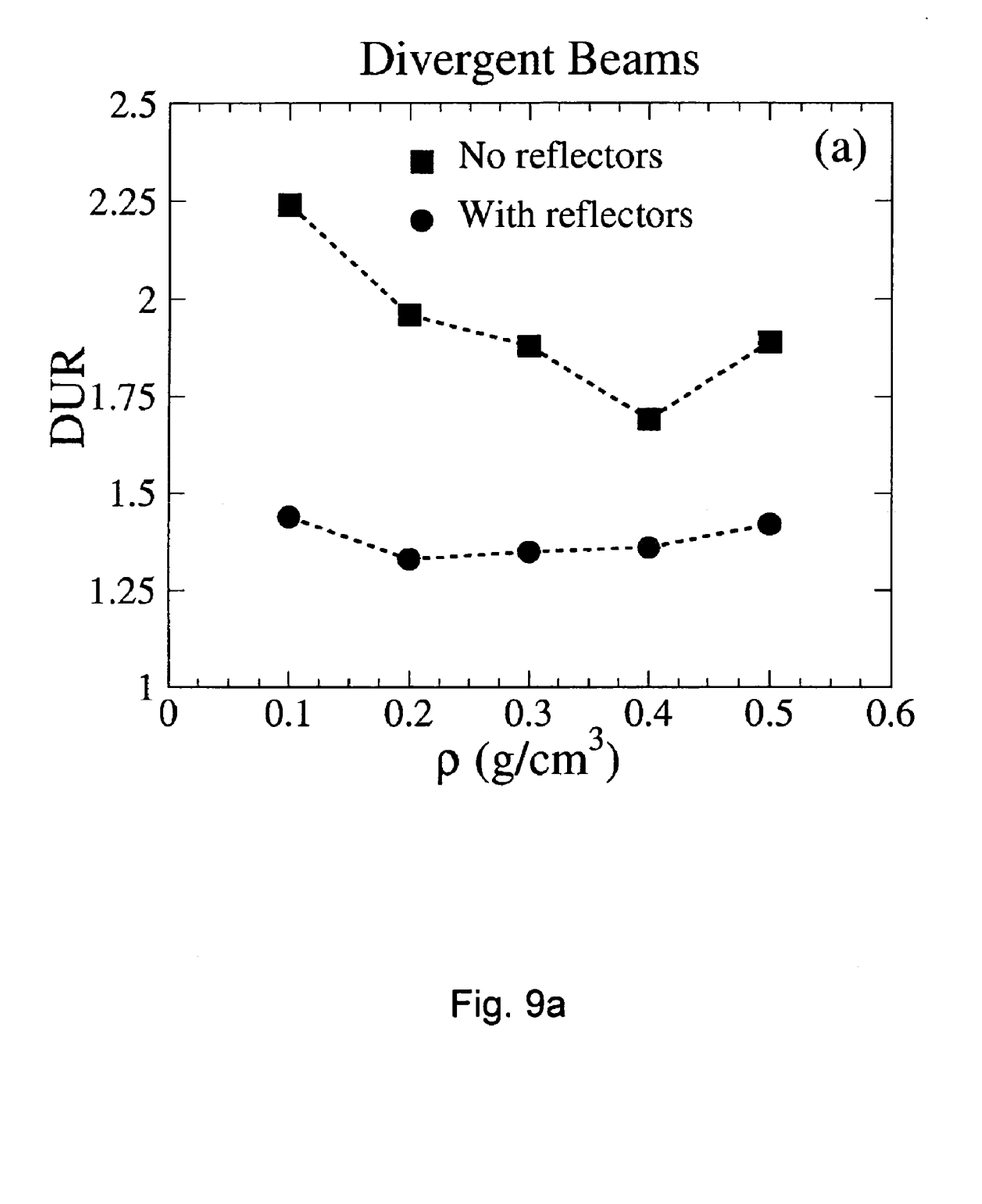
Figure 9B:
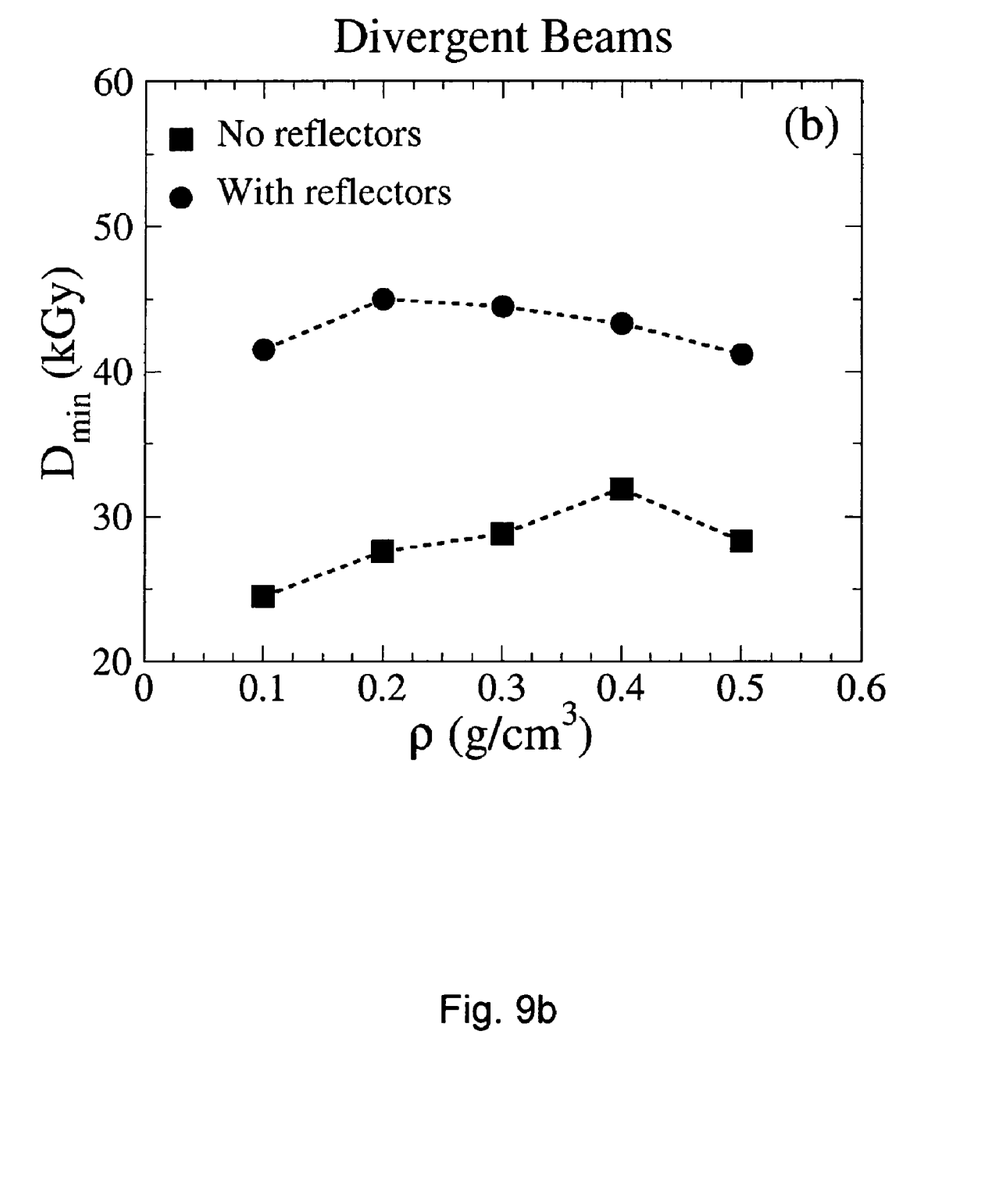

FIGS. 8a, 8b, 9a and 9b are DUR and Dmin curves obtained for the optimal values of the parameters d and α, i.e. 2 cm and 8°, as a function of the density of product packages, for a parallel and diverging electron beam, respectively. FIGS. 8a and 9a show that the improvement of the invention is obtained for a wide range of material densities, for a parallel beam as well as for a diverging beam. FIGS. 8b and 9b show that, in the same condition, the minimal dose obtained is much higher, i.e. the side-effect is reduced. Therefore, the minimal dose required for the product is obtained faster, and the throughput of the apparatus is higher.

An additional advantage of the invention is that the unwanted path of electrons in air can be minimised. The production of ozone can therefore be reduced.

In one embodiment, the reflectors may be attached to the scanning horn, or be part of it. In another embodiment, the reflectors may be attached to the conveyor, or be part of it. In still other embodiments, the reflectors may be attached to the ceiling, the floor, and/or one or several walls of the irradiation zone.

Guides may be attached to the conveyor or the reflectors to adjust the position of incoming product boxes. Those may be equipped with wheels to lower the rubbing of packages.

In one embodiment, the position and the angle of the reflectors may be fixed and not modifiable. In another embodiment, the position and/or angle are variable and may be linked to a treatment recipe. In still another embodiment, the position and/or angle may be modified manually but is not intended to be a processing parameter. The position may depend on the size of product units and/or scanning width. The angle may depend on the density of the product, height of product units and/or the scanning width.

Reflectors may be moved and/or tilted by means of rails, screws, chains, jacks or pistons. Ancillary equipments to move and/or tilt the reflectors will be suitable for work in high radiation and/or ozone environment. Alternatively, they can be isolated from such environment by means of shielding. In another embodiment, mechanical, electrical or electronic parts may be situated outside of the irradiation area.

Preferably, the reflectors and/or ancillary equipment should be easy to displace and/or remove in order to ease access and facilitate maintenance of any equipment in the irradiation area.

It will be apparent from the foregoing that, while particular forms of the invention have been illustrated and described, various modifications can be made without departing from the spirit and scope of the invention. Moreover, those skilled in the art will recognize that features shown in one embodiment may be utilized in another embodiment. In other instances, well-known equipment or process operations may be found missing in the embodiment descriptions. Those well known features have not been described in detail in order not to unnecessarily obscure the present invention.

The invention is not to be construed as limited to the above detailed description. More specifically, although the above description shows irradiation from above, the inven tion would equally apply to irradiation from the side, with reflectors located above and/or below the product.

The invention claimed is:

1. Apparatus for irradiating a product package, comprising a radiation source directing a radiation beam along a beam direction towards said product package, conveying means for transporting said product package past said radiation source along a transport path, reflecting means located on at least one side of the plane formed by said beam direction and said transport path, wherein the surface of the reflecting means are disposed at an angle of 1 to 15 degrees relative to said beam direction.

2. The apparatus according to claim 1, wherein the radiation source is an electron beam source.

3. The apparatus according to claim 1, further comprising means for adjusting the distance between the reflecting means and the transport path and/or the angle of the reflecting means with respect to the beam direction.

4. The apparatus according to claim 1, wherein said reflecting means consist of one or more rectangular metal sheets.

5. The apparatus according to claim 1, wherein said reflecting means comprises a plurality of scales.

6. The apparatus according to claim 5, wherein said scales are oriented perpendicularly to said beam direction.

7. The apparatus according to claim 1, wherein said reflecting means comprises means for cooling.

8. The apparatus according to claim 1, wherein said conveying means are provided with a gap under said radiation beam, and said reflecting means are positioned in said gap.

9. A method for irradiating product packages, comprising the steps of:
   providing a radiation source directing a radiation beam towards a transport path;
   providing reflecting means for reflecting part of said radiation beam towards said transport path;
   adjusting the angle of said reflecting means to said radiation beam;
   transporting said product package along said transport path, under said radiation beam, whereby part of said radiation beam is reflected by said reflecting means on sides of said product package.

10. The method according to claim 9, further comprising the step of adjusting the distance of said reflection means to said transport path according to the size of the product package, for minimizing the distance between said reflection means and said product package.

11. The method according to claim 9, wherein the product packages have a mean density comprised between 0.05 and 0.50 $g/cm^3$.

* * * * *